United States Patent [19]

Koyanagi et al.

[11] Patent Number: 5,708,175

[45] Date of Patent: Jan. 13, 1998

[54] PROCESS FOR PRODUCING 4-TRIFLUOROMETHYLNICOTINIC ACID

[75] Inventors: Toru Koyanagi; Tetsuo Yoneda; Fumio Kanamori; Shigehisa Kanbayashi; Toyoshi Tanimura; Noriyuki Horiuchi, all of Kusatsu, Japan

[73] Assignee: Ishihara Sangyo Kaisha Ltd., Osaka, Japan

[21] Appl. No.: 648,761

[22] Filed: May 16, 1996

[30] Foreign Application Priority Data

| May 26, 1995 | [JP] | Japan | 7-152364 |
| Aug. 8, 1995 | [JP] | Japan | 7-224728 |
| Oct. 18, 1995 | [JP] | Japan | 7-296248 |

[51] Int. Cl.$^6$ .................. C07D 213/12; C07D 213/08; C07D 213/80
[52] U.S. Cl. .................................... 546/250; 546/318
[58] Field of Search .......................... 546/250, 318

[56] References Cited

U.S. PATENT DOCUMENTS 5,360,806  11/1994  Toki et al. ........................... 514/318

OTHER PUBLICATIONS

Patent Abstracts of Japan, vol. 95, No. 4, May 31, 1995, JP-A-07 010841, Jan. 13, 1995.
Patent Abstracts of Japan, vol. 95, No. 4, May 31, 1995, JP-A-07 025853, Jan. 27, 1995.
Journal of Fluorine Chemistry, vol. 69, pp. 195-198, 1994, I.I. Gerus, et al., "β-Ethoxyvinyl Polyfluoroalkyl Ketones—Versatile Synthones in Fluoroorganic Chemistry".
Synthesis, pp. 483-486, Jun. 1991, Agenor Colla, et al., "Trihaloacetylated Enol Ethers—General Synthetic Procedure and Heterocycling Ring Closure Reactions with Hydroxylamine".
Chemische Berichte, vol. 122, pp. 1179-1186, 1989, M. Buback, et al., "Diastereoselectivity and Kinetics of Intermolecular Hetero Diels–Alder Reactions Under High Pressure. A Significant Pressure-Induced Increase in Stereoselectivity".
Chemistry Letters, pp. 499-502, 1976, M. Hojo, et al., "Electrophilic Substitutions of Olefinic Hydrogens II. Acylation of Vinyl Ethers and N-Vinyl Amides".
Tetrahedron Letters, vol. 30, No. 45, pp. 6173-6176, 1989, M. Hojo, et al., "O—N, S—N and N—N Exchange Reactions at Olefinic Carbon Atoms: Facile Synthetic Method for β-Trifluoroacetylvinylamines".
Zh. Org. Khim., vol. 26, No. 9, pp.1877-1883, 1990, I.I. Gerus, et al., ". . . Beta-Alkoxyvinyl . . . ".
Heterocycles, vol. 34, No. 7, pp. 1435-1441, 1992, E. Okada, et al., "A Facile and Convenient Synthetic Method for 3-Trifluoroacetyl-Pyrroles".
Synthesis, pp.. 533-535, Jun. 1992, E. Okada, et al., "A Facile and Convenient Synthetic Method for N-β-Trifluoroacetylvinyl Amino Acid Esters, Alpha-Aminoacetophenones and Aminoacetonitriles as Potentially Useful Precursors of Fluorine-Containing Pyrroles".
Synthesis, pp. 207-209, Mar. 1991, M.G. Gorbunova, et al., "4-Ethoxy-1,1,1-Trifluoro-3-Buten-2-One as a New Protecting Reagent in Peptide Synthesis".

Primary Examiner—Alan L. Rotman
Attorney, Agent, or Firm—Oblon, Spivak, McClelland, Maier & Neustadt, P.C.

[57] ABSTRACT

A process for producing 4-trifluoromethylnicotinic acid of the formula (VIII) or its salt:

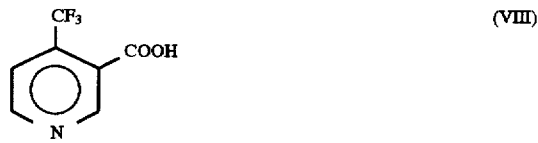

(VIII)

which comprises (i) a first step of reacting a halide of the formula (I):

CF$_3$COHal    (I)

wherein Hal is a halogen atom, with a compound of the formula (II):

CH$_2$=CHOR$^1$    (II)

wherein R$^1$ is an alkyl group, in the presence of a base to obtain a 4-alkoxy-1,1,1-trifluoro-3-buten-2-one of the formula (III):

CF$_3$CO—CH=CH—OR$^1$    (III)

wherein R$^1$ is as defined above, and reacting this compound with ammonia to obtain 4-amino-1,1,1-trifluoro-3-buten-2-one of the formula (IV):

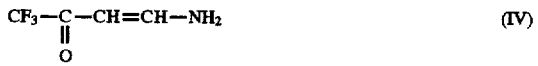

(IV)

and (ii) a second step of subjecting the 4-amino-1,1,1-trifluoro-3-buten-2-one obtained in the first step and a compound of the formula (V):

ACO$_2$R$^2$    (V)

wherein R$^2$ is an ester-forming residue, and A is (R$^3$O)CH=CH— or (R$^3$O)$_2$CHCH$_2$—, wherein R$^3$ is an alkyl group, to a condensation reaction to obtain a compound of the formula (VI) (inclusive of its salt):

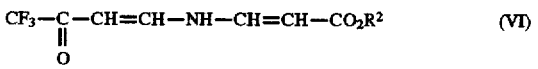

(VI)

wherein R$^2$ is as defined above, and/or a compound of the formula (VII) (inclusive of its salt):

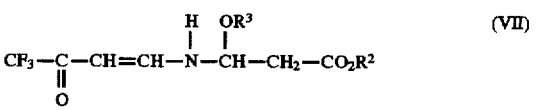

(VII)

wherein R$^2$ and R$^3$ are as defined above, as the reaction product, and then subjecting the reaction product to ring closure and hydrolysis.

13 Claims, No Drawings

PROCESS FOR PRODUCING 4-TRIFLUOROMETHYLNICOTINIC ACID

The present invention relates to a novel process for producing 4-trifluoromethylnicotinic acid of the after-mentioned formula (VIII) or its salt, which is useful as an active ingredient for agricultural chemicals or as a precursor for production of agricultural chemicals or pharmaceuticals.

As a process for producing 4-trifluoromethylnicotinic acid, (1) a process disclosed in U.S. Pat. No. 5,360,806 or (2) a process disclosed in Japanese Unexamined Patent Publication No. 10841/1995 is, for example, known. However, the former process is complex with many reaction steps and requires severe reaction conditions, and the latter process is also complex with many reaction steps. Accordingly, these processes are costly, and an improvement has been desired for industrial application.

Further, it is known from Chem. Lett. 1976, 499 that 4-ethoxy-1,1,1-trifluoro-3-buten-2-one used as a starting material for producing 4-trifluoromethylnicotinic acid in the present invention, can be obtained by reacting trifluoroacetic anhydride with ethyl vinyl ether. However, this reaction requires a long period of time of from 10 hours to 20 hours and further requires expensive trifluoroacetic anhydride, and it thus has difficulties for industrial application. Further, a process of aminating this 4-ethoxy-1,1,1-trifluoro-3-buten-2-one to produce 4-amino-1,1,1-trifluoro-3-buten-2-one is disclosed in Chem. Ber. 122 (1989) 1179 and Tetrahedron Letters (1989), 30 (45) 6173. However, to produce 4-amino-1,1,1-trifluoro-3-buten-2-one by a combination of these processes, it is necessary to isolate 4-ethoxy-1,1,1-trifluoro-3-buten-2-one, which makes the reaction process cumbersome and unsuitable as an industrial process.

Under these circumstances, it is an object of the present invention to provide a process for producing the desired compound in good yield under a mild reaction condition with a small number of reaction steps.

In a first aspect, the present invention provides a process for producing 4-trifluoromethylnicotinic acid of the formula (VIII) or its salt:

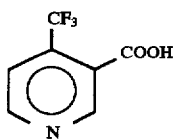  (VIII)

which comprises (i) a first step of reacting a halide of the formula (I):

CF₃COHal  (I)

wherein Hal is a halogen atom, with a compound of the formula (II):

CH₂=CHOR¹  (II)

wherein R¹ is an alkyl group, in the presence of a base to obtain a 4-alkoxy-1,1,1-trifluoro-3-buten-2-one of the formula (III):

CF₃CO—CH=CH—OR¹  (III)

wherein R¹ is as defined above, and reacting this compound with ammonia to obtain 4-amino-1,1,1-trifluoro-3-buten-2-one of the formula (IV):

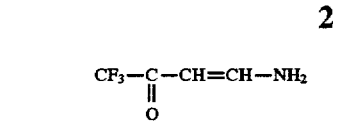  (IV)

and (ii) a second step of subjecting the 4-amino-1,1,1-trifluoro-3-buten-2-one obtained in the first step and a compound of the formula (V):

ACO₂R²  (V)

wherein R² is an ester-forming residue, and A is (R³O)CH=CH— or (R³O)₂CHCH₂—, wherein R³ is an alkyl group, to a condensation reaction to obtain a compound of the formula (VI) (inclusive of its salt):

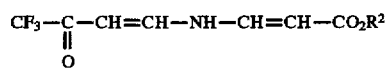  (VI)

wherein R² is as defined above, and/or a compound of the formula (VII) (inclusive of its salt):

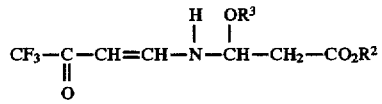  (VII)

wherein R² and R³ are as defined above, as the reaction product, and then subjecting the reaction product to ring closure and hydrolysis.

In a second aspect, the present invention provides a process for producing a 4-alkoxy-1,1,1-trifluoro-3-buten-2-one of the formula (III):

CF₃CO—CH=CH—OR¹  (III)

wherein R¹ is an alkyl group, which comprises reacting a halide of the formula (I):

CF₃COHal  (I)

wherein Hal is a halogen atom, with a compound of the formula (II):

CH₂=CHOR¹  (II)

wherein R¹ is as defined above, in the presence of a base.

In a third aspect, the present invention provides a process for producing 4-amino-1,1,1-trifluoro-3-buten-2-one, which comprises reacting a halide of the formula (I):

CF₃COHal  (I)

wherein Hal is a halogen atom, with a compound of the formula (II):

CH₂=CHOR¹  (II)

wherein R¹ is an alkyl group, in the presence of a base to obtain a 4-alkoxy-1,1,1-trifluoro-3-buten-2-one of the formula (III):

CF₃CO—CH=CH—OR¹  (III)

wherein R¹ is as defined above, and reacting this compound with ammonia.

In a fourth aspect, the present invention provides a process for producing 4-trifluoromethylnicotinic acid of the formula (VIII) or its salt:

$$\text{(VIII)}$$

[Structure: pyridine ring with CF₃ and COOH substituents]

which comprises subjecting 4-amino-1,1,1-trifluoro-3-buten-2-one of the formula (IV):

$$CF_3-\underset{\underset{O}{\|}}{C}-CH=CH-NH_2 \quad \text{(IV)}$$

and a compound of the formula (V):

$$ACO_2R^2 \quad \text{(V)}$$

wherein $R^2$ is an ester-forming residue, and A is $(R^3O)CH=CH-$ or $(R^3O)_2CHCH_2-$, wherein $R^3$ is an alkyl group, to a condensation reaction to obtain a compound of the formula (VI) (inclusive of its salt):

$$CF_3-\underset{\underset{O}{\|}}{C}-CH=CH-NH-CH=CH-CO_2R^2 \quad \text{(VI)}$$

wherein $R^2$ is as defined above, and/or a compound of the formula (VII) (inclusive of its salt):

$$CF_3-\underset{\underset{O}{\|}}{C}-CH=CH-\underset{\underset{}{|}}{\overset{H}{N}}-\overset{OR^3}{\underset{|}{CH}}-CH_2-CO_2R^2 \quad \text{(VII)}$$

wherein $R^2$ and $R^3$ are as defined above, as the reaction product, and then subjecting the reaction product to ring closure and hydrolysis.

Further, the present invention provides a novel compound of the formula (VI) or its salt and a novel compound of the formula (VII) or its salt, as intermediates for producing the compound of the formula (VIII).

Now, the present invention will be described in detail with reference to the preferred embodiments.

(1) First step

The halogen atom represented by Hal in the above formula (I) may be chlorine, fluorine, bromine or iodine. Among them, chlorine is preferred.

The alkyl group represented by $R^1$ in the above formulas (II) and (III) is a linear or branched alkyl group, preferably a $C_{2-4}$ alkyl group such as an ethyl group, a propyl group, an isopropyl group, a butyl group or a tert-butyl group, more preferably an ethyl group or a propyl group, most preferably an ethyl group.

The processes for producing a 4-alkoxy-1,1,1-trifluoro-3-buten-2-one relating to the first and second aspects of the present invention and 4-amino-1,1,1-trifluoro-3-buten-2-one relating to the first and third aspects of the present invention, will be described in detail.

First stage: Production of 4-alkoxy-1,1,1-trifluoro-=3-buten-2-one $$CF_3COHal + CH_2=CHOR^1 \xrightarrow{\text{base}}$$
$$\text{(I)} \quad \text{(II)}$$

$$CF_3CO-CH=CH-OR^1 + HHal$$
$$\text{(III)}$$

In the above formulas, $R^1$ is an alkyl group, and Hal is a halogen atom.

Second Stage: Amination of 4-alkoxy-1,1,1-trifluoro-3-buten-2-one $$CF_3CO-CH=CH-OR^1 + NH_3 \longrightarrow$$
$$\text{(III)}$$

$$CF_3CO-CH=CH-NH_2 + R^1OH$$
$$\text{(IV)}$$

In the above formulas, $R^1$ is an alkyl group.

The amounts of the halide of the formula (I) and the compound of the formula (II) used in the reaction of the first stage, can not generally be defined, since they vary depending upon the types of the compound of the formula (II), the base and the solvent, the reaction conditions, etc. However, the halide of the formula (I) is used usually in an amount of from 1.0 to 3.0 mols, preferably from 1.05 to 1.5 mols, per mol of the compound of the formula (II).

The reaction in the first stage is carried out usually in the presence of a base. The base to be used may, for example, be a nitrogen-containing heterocyclic compound such as pyridine, quinoline or picoline; or a tertiary base such as triethylamine, dimethylaniline, diethylaniline or 4-dimethylaminopyridine. Among them, pyridine, triethylamine, dimethylaniline, diethylaniline or 4-dimethylaminopyridine is preferred. Among them, pyridine is particularly preferred. These bases may be used alone or in combination as a mixture. The amount of the base used in the reaction of the first stage can not generally be defined, since it varies depending upon the types of the compound of the formula (II) and the solvent, the reaction conditions, etc. However, the base is used usually in an amount of from 1.0 to 3.0 equivalent weights, preferably from 1.05 to 1.5 equivalent weights, per mol of the compound of the formula (II).

In the reaction of the first stage, it is preferred to use a solvent. However, a solvent may not be used in a case where (1) the compound of the formula (II) is used in an excess amount, or (2) a base which serves also as a solvent, such as pyridine or triethylamine, is used. The solvent to be used may, for example, be an aromatic hydrocarbon such as benzene, toluene or xylene, an aliphatic hydrocarbon such as pentane or hexane; a halogenated hydrocarbon such as methylene chloride, chloroform or ethylene dichloride; or an ether such as diethyl ether, dibutyl ether or tetrahydrofuran. Among them, an aromatic hydrocarbon is preferred. Particularly preferred among them, is benzene or toluene. These solvents may be used alone or in combination as a mixture. The amount of the solvent used in the reaction of the first stage can not generally be defined, since it varies depending upon the reaction conditions, etc. However, the solvent is used usually in an amount of from 1 to 35 parts by weight, preferably from 3 to 16 parts by weight, per part by weight of the compound of the formula (II).

The reaction time for the reaction of the first stage varies depending upon the types of the compound of the formula (II), the solvent and the base, but it is usually within a range of from 1 to 12 hours, preferably from 2 to 6 hours.

The reaction temperature for the reaction of the first stage can not generally be defined, since it varies depending upon the types of the compound of the formula (II), the solvent and the base, etc. However, the reaction temperature is usually within a range of from $-20°$ C. to $+50°$ C., preferably from $0°$ C. to $+30°$ C.

Hydrogen halide formed by the reaction of the first stage will react with the base in the reaction solution to form a salt. Thus, the reaction solution after completion of the reaction of the first stage contains such as a salt in addition to the compound of the formula (III). In the first, second and third aspects of the present invention, the compound of the formula (III) as the reaction product, may be isolated from the reaction solution, but may be continuously subjected to the amination reaction of the second stage without isolation, to obtain the compound of the formula (IV) as the desired product according to the third aspect of the present invention. In either case, it is preferred to carry out pretreatment to remove the by-product salt from the solution containing the compound of the formula (III) in order to increase the yield of the compound of the formula (IV).

The method for removing the salt may, for example, be (1) a method of filtering off the salt by subjecting the reaction solution containing the compound of the formula (III) to filtration or (2) a method of removing the salt by extraction by adding water to the reaction solution containing the compound of the formula (III). For the extraction by the method (2), in addition to water, an organic solvent may be used in combination, as the case requires, whereby the compound of the formula (III) can efficiently be recovered in the organic layer. The organic solvent which can be used in combination for extraction, may, for example, be an aromatic hydrocarbon such as benzene, toluene or xylene; a halogenated hydrocarbon such as methylene chloride or chloroform; an ether such as diethyl ether or dibutyl ether; or an acetate such as methyl acetate or ethyl acetate. Among them, an aromatic hydrocarbon is preferred. Particularly preferred among them is benzene or toluene. After removal of the salt by extraction, the reaction solution containing the compound of the formula (III) is subjected to washing treatment, followed by drying to remove water. The drying is preferably carried out by using a drying agent such as anhydrous magnesium sulfate, anhydrous sodium sulfate or anhydrous calcium sulfate.

After the removal of the salt, other liquid component (such as the solvent) is distilled off from the reaction solution containing the compound of the formula (III) to isolate the compound of the formula (III) as the desired product according to the second aspect of the present invention.

Various conditions in the reaction of the first stage i.e. the amounts of the halide of the formula (I) and the compound of the formula (II), use or non-use of the base and the amount of the base to be used, use or non-use of the solvent, and the amount of the solvent to be used, the reaction temperature and the reaction time, may be appropriately selected and combined for use from the usual ranges and the preferred ranges for the respective conditions.

For the amination reaction of the second stage, various methods are conceivable. However, it is preferred to carry out the reaction by blowing ammonia gas into the reaction solution containing the compound of the formula (III). The amount of the ammonia gas to be used can not generally be defined, since it varies depending upon the reaction conditions, etc. However, the ammonia gas is used usually in an amount of from 1.0 to 10 mols, preferably from 1.0 to 5.0 mols, per mol of the compound of the formula (III).

In the above amination reaction, it is preferred to use a solvent. The solvent may, for example, be an aromatic hydrocarbon such as benzene, toluene or xylene; a halogenated hydrocarbon such as methylene chloride or chloroform; an ether such as diethyl ether, dibutyl ether or tetrahydrofuran; or an acetate such as methyl acetate or ethyl acetate. Among them, an aromatic hydrocarbon is preferred. Particularly preferred among them is benzene or toluene. These solvents may be used alone or in combination as a mixture. The amount of the solvent to be used in the amination reaction can not generally be defined, since it varies depending upon the reaction conditions, etc. However, the solvent is used usually in an amount of from 1 to 35 parts by weight, preferably from 3 to 16 parts by weight, per part by weight of the compound of the formula (III). In a case where the above solvent is already used in a predetermined amount in the reaction of the first stage, the same solvent can also be used for the amination reaction, and it is not necessary to use a fresh solvent. In a case where no solvent was used in the reaction of the first stage, the above solvent may be added to the reaction solution containing the compound of the formula (III) as the case requires.

The reaction temperature and the reaction time for the amination reaction can not generally be defined, since they vary depending upon the amount of the ammonia gas. However, the reaction temperature is usually from −10° C. to +50° C., preferably from 0° C. to 30° C., and the reaction time is usually from 10 minutes to 6 hours, preferably from 0.5 to 2 hours.

Various conditions in the amination reaction of the second stage i.e. the amounts of the compound of the formula (III) and the ammonia gas, use or non-use of a solvent and the amount of the solvent to be used, the reaction temperature, and the reaction time, may be selected and combined for use from the usual ranges and the preferred ranges for the respective conditions.

After completion of the amination reaction, 4-amino-1,1,1-trifluoro-3-buten-2-one of the formula (IV) as the desired product of the third aspect of the present invention can be obtained by subjecting the reaction product to conventional post-treatment such as solvent distillation, washing or drying.

(2) Second step

The ester-forming residue represented by $R^2$ in the formulas (V), (VI) and (VII) may, for example, be an alkyl group, an alkenyl group, an alkynyl group or a phenyl group. Preferred is an alkyl group. The compound of the formula (V) includes a compound of the formula (V-1):

wherein $R^2$ is an ester-forming residue, and $R^3$ is an alkyl group, and a compound of the formula (V-2):

wherein $R^2$ is an ester-forming residue, and $R^3$ is an alkyl group. In these compounds, the alkyl group for $R^2$ and the alkyl group for $R^3$ may, for example, be a linear or branched $C_{1-6}$ alkyl group, such as a methyl group, an ethyl group, a propyl group, an isopropyl group, a butyl group or a tert-butyl group, preferably a methyl group or an ethyl group, more preferably a methyl group. Further, the alkyl groups for $R^2$ and $R^3$ in the formula (V-1) or (V-2) may be the same or different, preferably the same.

Now, the process for producing 4-trifluoromethylnicotinic acid or its salt relating the first and fourth aspects of the present invention will be described in detail with reference to the reaction flow chart.

Condensation reaction

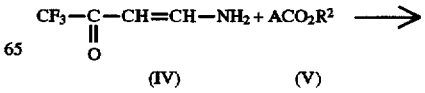

-continued

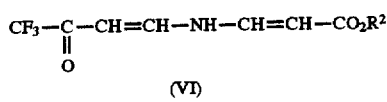

(VI)

and/or

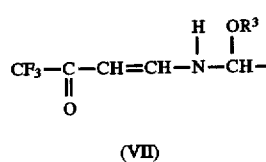

(VII)

Ring closure and hydrolysis (VI) and/or (VII) →  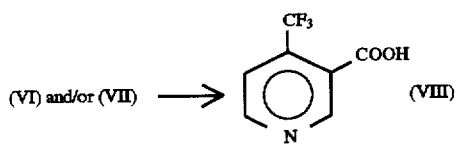 (VIII)

In the above formulas, $R^2$ is an ester-forming residue, and A is $(R^3O)CH=CH-$ or $(R^3O)_2CHCH_2-$, wherein $R^3$ is an alkyl group.

The amounts of the compounds of the formulas (IV) and (V) to be used in the condensation reaction can not generally be defined, since they vary depending upon the type of the compound of the formula (II), the reaction conditions which will be described below, etc. However, the compound of the formula (V) is used usually in an amount of from 1.0 to 1.2 mols, preferably from 1.02 to 1.06 mols, per mol of the compound of the formula (IV).

The reaction temperature and the reaction time for the condensation reaction can not generally be defined, since they vary depending upon the type of the compound of the formula (V), the reaction conditions which will be described below, etc. However, the reaction temperature is usually within a range of from −20° C. to +100° C., and the reaction time is usually within a range of from 0.1 to 12 hours, preferably from 0.3 to 6 hours.

As mentioned above, the compound of the formula (V) includes a compound of the formula (V-1) and a compound of the formula (V-2). The reaction conditions for the condensation reaction vary depending upon which compound is to be used, and such conditions will be described below.

Firstly, the reaction conditions for the condensation reaction which is carried out by using the compound of the formula (V-1) as the compound of the formula (V), will be described. In this case, the reaction temperature is preferably from −10° C. to +75° C., and in order to carry out the condensation reaction efficiently, the reaction is preferably conducted in the presence of a base. The base to be used may, for example, be an alkali metal hydride such as sodium hydride or potassium hydride; an alkyl lithium such as n-butyl lithium or t-butyl lithium; an alkali metal such as sodium or potassium; and an alkali metal hydroxide such as sodium hydroxide or potassium hydroxide; an alkoxide such as sodium methoxide, sodium ethoxide, potassium methoxide or potassium t-butoxide; or a basic heterocyclic compound such as pyridine or quinoline. Among them, an alkali metal hydride is preferred. Particularly preferred among them is sodium hydride. These bases may be used alone or in combination as a mixture. In this case, the amount of the base to be used can not be generally defined, since it varies depending upon the type of the compound of the formula (V-1), use or non-use of a solvent, the reaction conditions, etc. However, the base is used usually in an amount of from 1.0 to 1.2 equivalent weights, preferably from 1.02 to 1.06 equivalent weights, per mol of the compound of the formula (IV).

To carry out the condensation reaction of the compound of the formula (IV) with the compound of the formula (V-1) efficiently, it is preferred to carry out the reaction in the presence of a solvent. In the reaction, the solvent may be used in such a manner that (1) the compound of the formula (IV) and the compound of the formula (V-1) are dissolved in the respective solvents, so that the respective solutions are reacted, (2) one of the compounds is dissolved in a solvent, and the other compound is reacted to the resulting solution, or (3) a solution having a base dissolved in a solvent, is added to a reaction system having both compounds dissolved. The solvent to be used may, for example, be a polar aprotic solvent such as N,N-dimethylformamide or acetonitrile; a halogenated hydrocarbon such as methylene chloride or chloroform; an ether such as diethyl ether or tetrahydrofuran; an alcohol such as methanol or ethanol; or a basic heterocyclic compound such as pyridine or quinoline. Among them, a polar aprotic solvent is preferred. Particularly preferred among them is N,N-dimethylformamide. These solvents may be used alone or in combination as a mixture. The amount of the solvent to be used in the condensation reaction can not generally be defined, since it varies depending upon the type of the compound of the formula (V-1), use or non-use of the base, the reaction conditions, etc. However, the solvent is used usually in an amount of from 1 to 30 parts by weight, preferably from 4 to 15 parts by weight, per part by weight of the compound of the formula (IV).

In the condensation reaction of the compound of the formula (IV) with the compound of the formula (V-1), a compound of the formula (VI) or its salt will be formed via a compound of the formula (VII) or its salt. Namely, of the two $R^3O$ groups present in the compound of the formula (V-1), only one leaves first to form a compound of the formula (VII) or its salt. Thereafter, another $R^3O$ group remaining in the compound of the formula (VII) or its salt will leave to form the compound of the formula (VI) or its salt. That is, the following two stage reactions take place to form a compound of the formula (VI) (inclusive of its salt) and/or a compound of the formula (VII) (inclusive of its salt).

First stage

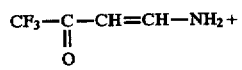

(IV)

(V-1)

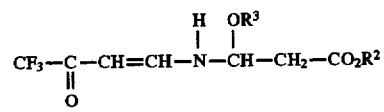

(VII)

Second stage (VII) 

-continued

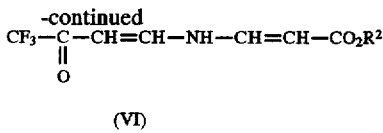

(VI)

In the above formulas, $R^2$ and $R^3$ are as defined above. To obtain the compound of the formula (VII) or its salt only, it is necessary to conduct the condensation reaction at a low temperature of from $-10°$ C. to $+30°$ C. for from 0.2 to 4 hours to let only the reaction of the first stage proceed completely. Further, to obtain the compound of the formula (VI) or its salt from the compound of the formula (VII) or its salt thus obtained, it is necessary to conduct the condensation reaction at a high temperature of from $40°$ to $75°$ C. for from 0.1 to 2 hours to let the reaction of the second stage proceed.

Now, with respect to a case where the condensation reaction is carried out by using the compound of the formula (V-2) as the compound of the formula (II), the reaction conditions will be described. The condensation reaction in this case is carried out in the presence of a base or an acid. The reaction in the presence of a base and the reaction in the presence of an acid are different from each other in the reaction mechanism, as will be described in detail.

When a compound of the formula (IV) and a compound of the formula (V-2) are subjected to a condensation reaction in the presence of a base, the reaction temperature is preferably from $-10°$ C. to $+65°$ C. Particularly when an alkali metal hydride or an alkyl lithium is used as a base, the reaction can be conducted at a normal temperature of from $0°$ to $30°$ C. The base to be used may, for example, be an alkali metal hydride such as sodium hydride or potassium hydride; an alkyl lithium such as n-butyl lithium or t-butyl lithium; an alkali metal such as sodium or potassium; an alkali metal hydroxide such as sodium hydroxide or potassium hydroxide; or an alkoxide such as sodium methoxide, sodium ethoxide, potassium methoxide or potassium t-butoxide. These bases may be used alone or in combination as a mixture.

By the condensation reaction of the compound of the formula (IV) and the compound of the formula (V-2) in the presence of the base, a compound of the formula (VI) or its salt will be formed via a compound of the formula (VII) or its salt. Namely, the reaction proceeds by the following reaction mechanism to form a compound of the formula (VI) (inclusive of its salt) and/or a compound of the formula (VII) (inclusive of its salt).

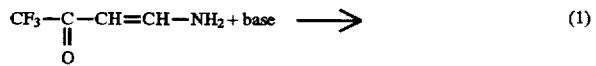 (1)

(IV)

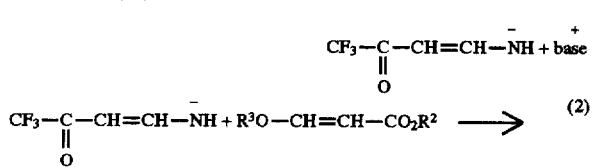 (2)

(V-2)

-continued

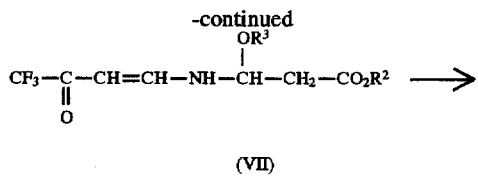

(VII)

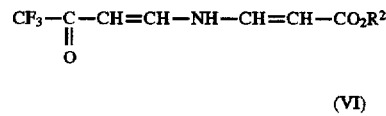

(VI)

In the above formulas, $R^2$ and $R^3$ are as defined above. Depending upon the difference in the reaction conditions, the resulting reaction product will be a compound of the formula (VI) or its salt, a compound of the formula (VII) or its salt, or a mixture thereof.

In a case where the compound of the formula (IV) and the compound of the formula (V-2) are subjected to a condensation reaction in the presence of an acid, the reaction is believed to proceed by the following reaction mechanism to form a compound of the formula (VI).

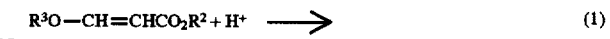 (1)

(V-2)

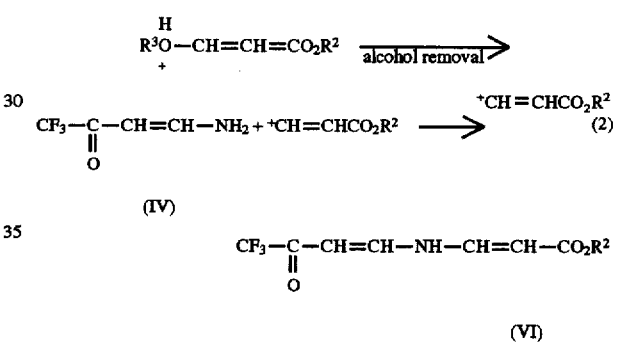

(IV)

In the above formulas, $R^2$ and $R^3$ are as defined above. The reaction temperature in this case is preferably from $-10°$ C. to $+100°$ C. The acid to be used may, for example, be an inorganic strong acid such as concentrated sulfuric acid, concentrated hydrochloric acid, concentrated nitric acid or phosphoric acid; or an organic strong acid such as methanesulfonic acid, p-toluenesulfonic acid or trifluoromethanesulfonic acid. These acids may be used alone or in combination as a mixture.

Among the above acids and bases, it is preferred to use an alkali metal hydride or an alkyl lithium, more preferably an alkali metal hydride, most preferably sodium hydride. In the condensation reaction wherein the compound of the formula (V-2) is used, the amount of the base or the acid to be used, can not generally be defined, since it varies depending upon the type of the compound of the formula (V-2), use or non-use of a solvent, the reaction conditions, etc. However, the base or the acid is used usually in an amount of from 1.0 to 1.2 equivalent weights, preferably from 1.02 to 1.06 equivalent weights, per mol of the compound of the formula (IV).

To carry out the condensation reaction of the compound of the formula (IV) with the compound of the formula (V-2) efficiently, it is preferred to conduct the reaction in the presence of a solvent. In the reaction, the solvent may be used in such a manner that (1) the compound of the formula (IV) and the compound of the formula (V-2) are, respectively, dissolved in a solvent, so that the respective solutions will be reacted, (2) either one of the compounds is dissolved in a solvent, and the other compound will be reacted to the resulting solution, or (3) both compounds are dissolved in a solvent to form a solution, which will be reacted with a solution having the acid or the base dissolved in a solvent. The solvent to be used may, for example, be a polar aprotic solvent such as N,N-dimethylformamide or acetonitrile; a halogenated hydrocarbon such as methylene chloride or chloroform; an ether such as diethyl ether or tetrahydrofuran; an alcohol such as methanol or ethanol; an aromatic hydrocarbon such as benzene or toluene; or a basic heterocyclic compound such as pyridine or quinoline. Among them, a polar aprotic solvent is preferred. Particularly preferred among them is N,N-dimethylformamide. These solvents may be used alone or in combination as a mixture. When a polar aprotic solvent is used in combination with at least one solvent selected from the group consisting of halogenated hydrocarbons, ethers and aromatic hydrocarbons, it is possible to obtain substantially the same level of effects as in a case where the polar aprotic solvent is used alone. Among such combinations of solvents, it is particularly preferred to use a combination of N,N-dimethylformamide and toluene in a ratio within a range of from 1:100 to 100:1, preferably from 2:1 to 4:1. The amount of the solvent to be used in the condensation reaction can not generally be defined, since it varies depending upon the type of the compound of the formula (V), use or non-use of a base, the reaction conditions, etc. However, the solvent is used usually in an amount of from 1 to 30 parts by weight, preferably from 4 to 15 parts by weight, per part by weight of the compound of the formula (IV).

The above-mentioned various conditions in the condensation reaction i.e. the amounts of the compound of the formula (IV) and the compound of the formula (V) and the reaction conditions, the reaction temperature and the reaction time, which vary depending upon the type of the compound of the formula (V), may be suitably selected and combined from the usual ranges and the preferred ranges for the respective conditions.

When the above condensation reaction is carried out in the presence of a base containing an alkali metal, the compound of the formula (VI) will form a salt as follows:

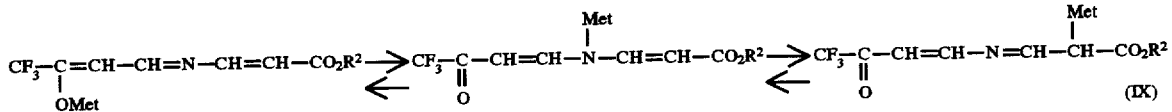

In the above formulas, Met is an alkali metal element, and $R^2$ is as defined above. Likewise, the compound of the formula (VII) will form a salt as follows:

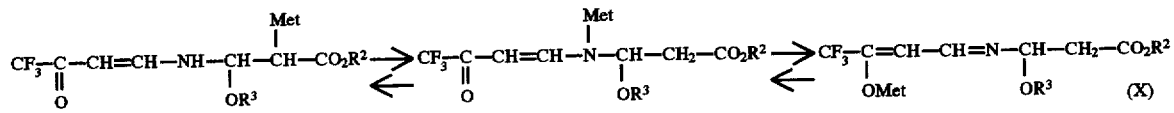

In the above formulas, Met, $R^2$ and $R^3$ are as defined above. Therefore, these salts may sometimes be contained in the reaction product of the condensation reaction. In such a case, after completion of the condensation reaction, the reaction product may be subjected to neutralization treatment with a mineral acid such as hydrochloric acid or sulfuric acid, whereby the compound of the formula (VI) and/or the compound of the formula (VII) can be obtained in good yield.

The compound of the formula (VI) and/or the compound of the formula (VII) can be isolated by subjecting it to post-treatment such as solid-liquid separation, washing and drying after completion of the condensation reaction. Further, the compound of the formula (VI) has the following tautomers and is likely to be isomerized especially in a solvent.

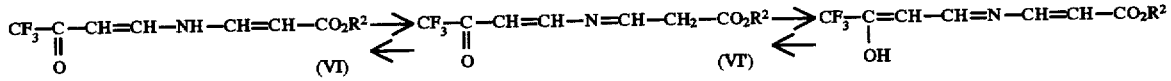

In the above formulas, $R^2$ is as defined above. Accordingly, the isolated compound of the formula (VI) may sometimes contain a compound of the formula (VI'):

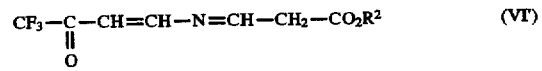

wherein $R^2$ is as defined above. Likewise, the compound of the formula (VII) has the following tautomers.

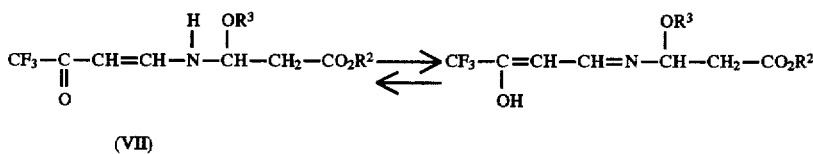

(VII)

In the above formulas, $R^2$ and $R^3$ are as defined above.

To carry out the ring closure and the hydrolysis of the product of the condensation reaction efficiently, it is preferred to conduct the reaction in the presence of a base. The base to be used here may, for example, be an alkali metal such as sodium or potassium; an alkali metal hydroxide such as sodium hydroxide or potassium hydroxide; an alkoxide such as sodium methoxide, sodium ethoxide, potassium methoxide or potassium t-butoxide; or a basic heterocyclic compound such as pyridine or quinoline. Among them, an alkali metal, an alkali metal alkoxide or an alkali metal hydroxide is preferred. Particularly preferred among them is sodium or sodium methoxide. These bases may be used alone or in combination as a mixture. The amount of the base to be used in the ring closure and the hydrolysis can not generally be defined, since it varies depending upon use or non-use of a solvent, the reaction conditions, etc. However, the base is used usually in an amount of from 0.2 to 2.0 equivalent weights, preferably from 0.5 to 1.2 equivalent weights, per mol of the product of the condensation reaction.

Further, to carry out the ring closure and the hydrolysis efficiently, it is preferred to conduct the reaction in the presence of a solvent. In the reaction, the solvent may be used in such a manner that (1) the reaction is carried out in the solvent, or (2) the solvent is added to the reaction system for the reaction. The solvent to be used, may, for example be water; or an alcohol such as methanol or ethanol. These solvents may be used alone or in combination as a mixture. Among the solvents, alcohols are preferred. Particularly preferred among them is methanol or ethanol. The amount of the solvent to be used for the ring closure and the hydrolysis, can not generally be defined, since it varies depending upon use or non-use of a base, the reaction conditions, etc. However, the solvent is used usually in an amount of from 1 to 30 parts by weight, preferably from 4 to 15 parts by weight, per part by weight of the product of the condensation reaction.

The reaction temperature and the reaction time for the ring closure and the hydrolysis can not generally be defined, since they vary depending upon use or non-use of a solvent or a base, the type of such a solvent or a base, etc. However, the reaction temperature is usually within a range of from 0° to 120° C., preferably from 10° to 80° C., and the reaction time is usually within a range of from 1 to 24 hours, preferably from 2 to 16 hours.

In the ring closure and the hydrolysis, the compound of the formula (VIII) will be formed via a cyclic carboxylate. Namely, the ring closure and the hydrolysis comprise two stage reactions i.e. a ring closure reaction for forming a cyclic carboxylate from the product of the condensation reaction and a hydrolysis reaction to obtain the compound of the formula (VIII) from the cyclic carboxylate. To obtain the compound of the formula (VIII) in good yield, it is preferred that the ring closure reaction is permitted to proceed completely to obtain the cyclic carboxylate, whereupon this cyclic carboxylate is subjected to hydrolysis in the presence of water, an alcohol or a mixture thereof, preferably water.

The above-mentioned various conditions for the ring closure and the hydrolysis i.e. use or non-use of the base and the solvent, the amounts thereof, the reaction temperature and the reaction time, can suitably be selected and combined from the usual ranges and the preferred ranges for the respective conditions.

Selection and combination of the various conditions for the above condensation reaction can further be suitably selected and combined in view of the selection and combination of various conditions for the ring closure and the hydrolysis.

The 4-trifluoromethylnicotinic acid of the formula (VIII) as the desired compound in the first and fourth aspects of the present invention, can be isolated by subjecting the reaction product to usual post-treatment such as solid-liquid separation, washing and drying after completion of the ring closure and the hydrolysis.

Now, some specific embodiments of the present invention will be described. However, it should be understood that the present invention is by no means restricted by such specific embodiments.

(1) A process for producing 4-trifluoromethylnicotinic acid of the formula (VIII) or its salt:
which comprises (i) a first step of reacting a halide of the formula (I) with a compound of the formula (II) in the presence of a base to obtain a 4-alkoxy-1,1,1-trifluoro-3-buten-2-one of the formula (III):

wherein $R^1$ is as defined above, and reacting this compound with ammonia to obtain 4-amino-1,1,1-trifluoro-3-buten-2-one, and (ii) a second step of subjecting the 4-amino-1,1,1-trifluoro-3-buten-2-one obtained in the first step and a compound of the formula (V) to a condensation reaction to obtain a compound of the formula (VI) (inclusive of its salt) and/or a compound of the formula (VII) (inclusive of its salt), as the reaction product, and then subjecting the reaction product to ring closure and hydrolysis.

(2) A process for producing a 4-alkoxy-1,1,1-trifluoro-3-buten-2-one, which comprises reacting a halide of the formula (I) with a compound of the formula (II) in the presence of a base.

(3) A process for producing a 4-amino-1,1,1-trifluoro-3-buten-2-one, which comprises reacting a halide of the formula (I) with a compound of the formula (II) to obtain a 4-alkoxy-1,1,1-trifluoro-3-buten-2-one of the formula (III):

wherein $R^1$ is as as defined above, and reacting this compound with ammonia.

(4) A process for producing 4-trifluoromethylnicotinic acid of the formula (VIII) or its salt, which comprises subjecting a compound of the formula (IV) and a compound of the formula (V) to a condensation reaction to obtain a compound of the formula (VI) (inclusive of its salt) and/or a compound of the formula (VII) (inclusive of its salt), as the reaction product, and then subjecting the reaction product to ring closure and hydrolysis.

(5) The process according to (1), (2) or (3), wherein the halide of the formula (I) is trifluoroacetyl chloride.

(6) The process according to (1), (3) or (5), wherein the compound of the formula (III) is reacted with ammonia without isolation.

(7) The process according to (1), (3), (5) or (6), wherein the ammonia to be used for the reaction is ammonia gas.

(8) The process according to (1), (2), (3), (5), (6) or (7), wherein a solvent is used for the reaction of the halide of the formula (I) with the compound of the formula (II).

(9) The process according to (1) or (4), wherein the compound of the formula (IV) and a compound of the formula (V-1) are subjected to the condensation reaction.

(10) The process according to (1) or (4), wherein the compound of the formula (IV) and a compound of the formula (V-2) are subjected to the condensation reaction in the presence of a base or an acid.

(11) The process according to (9), wherein the condensation reaction is carried out in the presence of a base and/or a solvent.

(12) The process according to (10), wherein the condensation reaction is carried out in the presence of a solvent.

(13) The process according to (1), (4), (9), (10), (11) or (12), wherein the ring closure and the hydrolysis are carried out in the presence of a base and/or a solvent.

(14) The process according to (1), (4), (9), (10), (11), (12) or (13), wherein in the condensation reaction, the compound of the formula (V) is used in an amount of from 1.0 to 1.2 mols, per mol of the compound of the formula (IV).

(15) A compound of the formula (VI) or its salt.

(16) A compound of the formula (VI) or its salt.

(17) A compound of the formula (VII) or its salt.

(18) The process according to (1), (2), (3) or (5), wherein the reaction temperature for the reaction of the halide of the formula (I) with the compound of the formula (II), is within a range of from −20° C. to +50° C.

(19) The process according to (1), (3), (5), (6) or (7), wherein the reaction temperature for the reaction of the compound of the formula (III) with ammonia, is within a range of from −10° C. to +50° C.

(20) The process according to (1), (3) or (5), wherein the salt formed as a by-product by the reaction of the halide of the formula (I) with the compound of the formula (II) in the presence of a base, is removed from the reaction solution containing the compound of the formula (III).

(21) A process for producing 4-amino-1,1,1-trifluoro-3-buten-2-one of the formula (IV), which comprises reacting a halide of the formula (I) with a compound of the formula (II) in the presence of a base, extracting and removing the salt formed as a by-product by the reaction, with water to obtain a reaction solution, blowing ammonia gas into this reaction solution to aminate the compound of the formula (III).

(22) A process for producing 4-amino-1,1,1-trifluoro-3-buten-2-one of the formula (IV), which comprises reacting a halide of the formula (I) with a compound of the formula (II) in a solvent in the presence of a base, extracting and removing a salt formed as a by-product by the reaction, with water to obtain a reaction solution, blowing ammonia gas into this reaction solution to aminate the compound of the formula (III).

(23) A process for producing 4-amino-1,1,1-trifluoro-3-buten-2-one of the formula (IV), which comprises reacting a halide of the formula (I) with a compound of the formula (II) in the presence of a base, extracting and removing a salt formed as a by-product by the reaction, with water to obtain a reaction solution, distilling off the solvent from the reaction solution to isolate the compound of the formula (III), and then aminating the compound.

(24) A process for producing a compound of the formula (VI) (inclusive of its salt) and/or a compound of the formula (VII) (inclusive of its salt), which comprises subjecting a compound of the formula (IV) and a compound of the formula (V) to a condensation reaction.

(25) The process according to (24), wherein the compound of the formula (IV) and a compound of the formula (V-1) are subjected to the condensation reaction.

(26) The process according to (24), wherein the compound of the formula (IV) and a compound of the formula (V-2) are subjected to the condensation reaction in the presence of a base or an acid.

(27) The process according to (9) or (25), wherein in the condensation reaction, the compound of the formula (V-1) is reacted in an amount of from 1.0 to 1.2 mols, per mol of the compound of the formula (IV) in the presence of a base or a solvent at a temperature within a range of from −10° C. to +30° C., to form a compound of the formula (IV), and then reacting it at a high temperature of from 40° to 75° C. to obtain a compound of the formula (VI) or its salt.

(28) A process for producing 4-trifluoromethylnicotinic acid of the formula (VIII) or its salt, which comprises subjecting a compound of the formula (VI) (inclusive of its salt) and/or a compound of the formula (VII) (inclusive of its salt) to ring closure and hydrolysis.

(29) The process according to (28), wherein the ring closure and the hydrolysis are carried out in the presence of a base and/or a solvent.

(30) The process according to (4) or (28), wherein in the ring closure and the hydrolysis, the compound of the formula (VI) and/or the compound of the formula (VII) is subjected to a ring closure reaction at a temperature of from 50° to 120° C. in the presence of a base and an alcohol to form a cyclic carboxylate, and the cyclic carboxylate is subjected to hydrolysis in the presence of water, an alcohol or a mixture thereof.

In specific embodiments for the first, second and third aspects of the present invention, various conditions for the above-mentioned reaction for producing a 4-alkoxy-1,1,1-trifluoro-3-buten-2-one and various conditions for the amination reaction of such a compound, can suitably be combined for use.

Further, in specific embodiments for the first and fourth aspects of the present invention, the above-mentioned various conditions i.e. (1) the base and/or the solvent in the condensation reaction, (2) the base and/or the solvent in the ring closure and the hydrolysis, (3) the amounts of the compound of the formula (IV) and the compound of the formula (V), (4) the temperature for the condensation reaction, and the temperatures for the ring closure and the hydrolysis, may suitably be combined for use.

Further, preferred as the compound of the formula (VI) or its salt, as an intermediate of the present invention, is an N-2-alkoxycarbonylvinyl 4,4,4-trifluoro-3-oxo-1-butenylamine or its salt. Particularly preferred among them is N-2-methoxycarbonylvinyl 4,4,4-trifluoro-3-oxo-1-butenylamine, N-2-ethoxycarbonylvinyl 4,4,4-trifluoro-3-oxo-1-butenylamine, or a salt thereof.

Further, preferred as the compound of the formula (VII) or its salt, as an intermediate of the present invention, is an N-1-alkoxy-2-alkoxycarbonylethyl 4,4,4-trifluoro-3-oxo-1-butenylamine or its salt. Particularly preferred among them is N-1-methoxy-2-methoxycarbonylethyl 4,4,4-trifluoro-3-oxo-1-butenylamine, N-1-ethoxy-2-ethoxycarbonylethyl 4,4,4-trifluoro-3-oxo-1-butenylamine or a salt thereof.

Now, the present invention will be described in further detail with reference to Examples. However, it should be understood that the present invention is by no means restricted to such specific Examples.

EXAMPLE 1

(1) Preparation of 4-ethoxy-1,1,1-trifluoro-3-buten-2-one

In 150 ml of toluene, 20 ml (0.21 mol) of ethyl vinyl ether and 18.2 g (0.23 mol) of pyridine were dissolved, and the solution was cooled with ice to a temperature of from +2° C. to +5° C.

Into this solution, 30.5 g (0.23 mol) of trifluoroacetyl chloride was blown over a period of 30 minutes. The mixture was stirred under cooling with ice at a temperature of from +2° C. to +5° C. further for 2.5 hours. Then, the reaction solution was extracted by an addition of 100 ml of toluene and 100 ml of ice water.

The organic layer was washed with water and a saturated sodium chloride aqueous solution and then dried by an addition of anhydrous magnesium sulfate. It was confirmed by gas chromatography that this solution contained 4-ethoxy-1,1,1-trifluoro-3-buten-2-one.

(2) Preparation of 4-amino-1,1,1-trifluoro-3-buten-2-one

From the toluene solution obtained in the above step, anhydrous magnesium sulfate was filtered off. Then, the solution was cooled with ice to a temperature of from +2° C. to +5° C. Under cooling with ice at a temperature of from +2° C. to +5° C., dry ammonia gas was blown into the solution for 30 minutes. After completion of the blowing, the reaction solution was returned to room temperature and further stirred for 30 minutes. After completion of the reaction, the solvent and formed ethanol were distilled off under reduced pressure, and the residue was distilled under vacuum to obtain 24.5 g (yield: 84%) of the desired product showing a boiling point of 65° C./2 mmHg.

EXAMPLE 2

(1) Preparation of 4-ethoxy-1,1,1-trifluoro-3-buten-2-one

In 150 ml of methylene chloride, 21 ml (0.22 mol) of ethyl vinyl ether and 26.1 g (0.33 mol) of pyridine were dissolved, and 43.8 g (0.33 mol) of trifluoroacetyl chloride was blown into this solution over a period of 30 minutes at room temperature. The mixture was further stirred at room temperature for 2.5 hours. Then, the reaction solution was extracted by an addition of 100 ml of methylene chloride and 100 ml of ice water.

The organic layer was washed with water and a saturated sodium chloride aqueous solution and then dried by an addition of anhydrous magnesium sulfate. It was confirmed by gas chromatography that this solution contained 4-ethoxy-1,1,1-trifluoro-3-buten-2-one.

(2) Preparation of 4-amino-1,1,1-trifluoro-3-buten-2-one

From the methylene chloride solution obtained in the above step, anhydrous magnesium sulfate was filtered off, and then, the solution was cooled with ice to a temperature of from +2° C. to +5° C. Under cooling with ice at a temperature of from +2° C. to +5° C., dry ammonia gas was blown into the solution for 30 minutes. After completion of the blowing, the reaction solution was stirred for further 30 minutes while returning it to room temperature.

After completion of the reaction, the solvent and the formed ethanol were distilled off under reduced pressure, and the residue was distilled under vacuum to obtain 21.4 g (yield: 70%) of the desired product.

EXAMPLE 3

15.0 g (yield: 49%) of the desired product was prepared in the same manner as in Example 2 except that instead of 26.1 g (0.33 mol) of pyridine, 33.4 g (0.33 mol) of triethylamine was used.

EXAMPLE 4

19.3 g (yield: 63%) of the desired product was obtained in the same manner as in Example 2 except that instead of 26.1 g (0.33 mol) of pyridine, 40.0 g (0.33 mol) of N,N-dimethylaniline was used.

EXAMPLE 5

(1) Preparation of 4-ethoxy-1,1,1-trifluoro-3-buten-2-one

In 150 ml of ethylene dichloride, 21 ml (0.22 mol) of ethyl vinyl ether and 26.1 g (0.33 mol) of pyridine were dissolved, and the solution was cooled with ice to a temperature of from 15° to 20° C.

Into this solution, 43.8 g (0.33 mol) of trifluoroacetyl chloride was blown over a period of 30 minutes at a temperature of from 15° to 20° C. After completion of the blowing, the reaction solution was further stirred for 2.5 hours while returning the reaction solution to room temperature. Then, the reaction solution was extracted by an addition of 100 ml of ethylene dichloride and 100 ml of ice water.

The organic layer was washed with water and a saturated sodium chloride aqueous solution and then dried by an addition of anhydrous magnesium sulfate. It was confirmed by gas chromatography that this solution contained 4-ethoxy-1,1,1-trifluoro-3-buten-2-one.

(2) Preparation of 4-amino-1,1,1-trifluoro-3-buten-2-one

From the ethylene dichloride solution obtained in the above step, anhydrous magnesium sulfate was filtered off. Then, the solution was cooled with ice to a temperature of from +2° C. to +5° C. Under cooling with ice at a temperature of from +2° C. to +5° C., dry ammonia gas was blown into the solution for 30 minutes. After completion of the blowing, the reaction solution was further stirred for 30 minutes while returning it to room temperature.

After completion of the reaction, the solvent and the formed ethanol were distilled off under reduced pressure, and the residue was distilled under vacuum to obtain 22.0 g (yield: 72%) of the desired product.

EXAMPLE 6

(1) Preparation of 4-butoxy-1,1,1-trifluoro-3-buten-2-one

In 150 ml of toluene, 28 ml (0.22 mol) of n-butyl vinyl ether and 26.1 g (0.33 mol) of pyridine were dissolved, and the solution was cooled with ice to a temperature of from 10° to 15° C.

To this solution, 43.8 g (0.33 mol) of trifluoroacetyl chloride was blown over a period of 30 minutes at a temperature of from 15° to 20° C. After completion of the blowing, the reaction solution was further stirred for 2.5 hours, while returning it to room temperature. Then, the reaction solution was extracted by an addition of 100 ml of toluene and 100 ml of ice water.

The organic layer was washed with water and a saturated sodium chloride aqueous solution and then dried by an addition of anhydrous magnesium sulfate. It was confirmed by gas chromatography that this solution contained 4-butoxy-1,1,1-trifluoro-3-buten-2-one.

(2) Preparation of 4-amino-1,1,1-trifluoro-3-buten-2-one

From the toluene solution obtained in the above step, anhydrous magnesium sulfate was filtered off. Then, the solution was cooled with ice to a temperature of from 2° C. to +5° C. Under cooling with ice at a temperature of from +2° C. to +5° C., dry ammonia gas was blown into the solution for 30 minutes. After completion of the blowing, the reaction solution was further stirred for 30 minutes, while returning it to room temperature.

After completion of the reaction, the solvent and the formed n-butanol were distilled off under reduced pressure, and the residue was distilled under vacuum to obtain 18.7 g (yield: 61%) of the desired product.

EXAMPLE 7

(1) Step of condensation reaction 11.18 g (0.076 mol) of methyl 3,3-dimethoxypropionate and 3.04 g (0.076 mol) of sodium hydride (60% oil suspension) were added to 65 ml of N,N-dimethylformamide, followed by cooling with ice. Then, 10.0 g (0.072 mol) of 4-amino-1,1,1-trifluoro-3-buten-2-one was gradually dropwise added thereto. After completion of the dropwise addition, the reaction solution was reacted with stirring for 2 hours, while returning it to room temperature. Then, the reaction solution was heated to 50° C. and further reacted for one hour.

After completion of the reaction, the obtained reaction solution was poured into 300 ml of ice water and then neutralized by an addition of concentrated hydrochloric acid. The precipitate was collected by filtration and washed with cool water to obtain 12.06 g (yield: 75%) of N-2-methoxycarbonylvinyl 4,4,4-trifluoro-3-oxo-1-butenylamine (melting point: 93.0°–95.3° C.).

(2) Step of ring closure and hydrolysis 0.87 g (0.038 mol) of metal sodium was dissolved in 200 ml of methanol, and to this solution, 12.06 g (0.54 mol) of N-2-methoxycarbonylvinyl 4,4,4-trifluoro-3-oxo-1-butenylamine obtained by the above condensation reaction, was added, and the mixture was reacted with stirring for 12 hours under heating and refluxing. Methanol was distilled off under reduced pressure. Then, 50 ml of water and 1.0 g (0.025 mol) of sodium hydroxide were added to the residue, and the mixture was further reacted with stirring at room temperature for 2 hours. After completion of the reaction, extraction was carried out by an addition of 50 ml of diethyl ether. The aqueous layer was acidified (pH 1 to 2) with concentrated hydrochloric acid, and the mixture was again extracted by an addition of 200 ml of diethyl ether. The ether layer was dried over anhydrous magnesium sulfate. Then, the solvent was distilled off under reduced pressure to obtain 7.61 g (yield: 74%) of 4-trifluoromethylnicotinic acid (melting point: 147°–149° C.).

EXAMPLE 8

Step of condensation reaction 5.63 g (0.038 mol) of methyl 3,3-dimethoxypropionate and 1.52 g (0.038 mol) of sodium hydride (60% oil suspension) were added to 28 ml of N,N-dimethylformamide. To this mixture, a solution having 5.0 g (0.036 mol) of 4-amino-1,1,1-trifluoro-3-buten-2-one dissolved in 5 ml of N,N-dimethylformamide, was gradually dropwise added. After completion of the dropwise addition, the reaction mixture was reacted at 65° C. for 20 minutes.

After completion of the reaction, the obtained reaction solution was poured into 150 ml of ice water and then neutralized by an addition of concentrated hydrochloric acid. The precipitate was collected by filtration and washed with cool water to obtain 4.09 g (yield: 51%) of N-2-methoxycarbonylvinyl 4,4,4-trifluoro-3-oxo-1-butenylamine.

EXAMPLE 9

Step of condensation reaction 4.53 g (0.11 mol) of sodium hydride (60% oil suspension) was suspended in 100 ml of N,N-dimethylformamide, and the suspension was cooled with ice to 5° C. Then, a solution having 15.0 g (0.11 mol) of 4-amino-1,1,1-trifluoro-3-buten-2-one and 13.14 g (0.11 mol) of methyl 3-methoxyacrylate dissolved in 20 ml of N,N-dimethylformamide, was dropwise added thereto over a period of 30 minutes with vigorous stirring under cooling with ice at a temperature of from 5° to 10° C. After completion of the dropwise addition, the solution was further reacted for 2.5 hours under cooling with ice at a temperature of from 5° to 10° C.

After completion of the reaction, the obtained reaction solution was poured into 500 ml of ice water and then neutralized by an addition of concentrated hydrochloric acid with vigorous stirring. The precipitate was collected by filtration and washed with cool water to obtain crystals, which were dried under reduced pressure at 50° C. to obtain 19.98 g (yield: 83%) of the reaction product having a melting point of 92.0° C.

The reaction product having a melting point of 92.0° C. thus obtained, was dissolved in deutero-chloroform, and NMR was measured, whereby in addition to the peak for N-2-methoxycarbonylvinyl 4,4,4-trifluoro-3-oxo-1-butenylamine, a peak for N-2-methoxycarbonylethylidene 4,4,4-trifluoro-3-oxo-2-butenylamine, was detected.

EXAMPLE 10

Step of condensation reaction 1.50 g (10.8 mmol) of 4-amino-1,1,1-trifluoro-3-buten-2-one and 1.31 g (11.3 mmol) of methyl 3-methoxyacrylate were dissolved in 15 ml of N,N-dimethylformamide, and 1.70 g (11.3 mmol) of trifluoromethanesulfonic acid was added to this solution at room temperature. Then, this solution was reacted for one hour with stirring in an oil bath at 90° C.

After completion of the reaction, the obtained reaction solution was poured into 100 ml of ice water and extracted with diethyl ether. The organic layer was dried over anhydrous sodium sulfate, and the solvent was distilled off under reduced pressure. Then, the residue was purified by silica gel column chromatography to obtain 1.25 g (yield: 51.9%) of the reaction product. The obtained reaction product was confirmed to be identical with the reaction product of Example 9 by gas chromatography.

EXAMPLE 11

Step of condensation reaction 1.50 g (10.8 mmol) of 4-amino-1,1,1-trifluoro-3-buten-2-one and 1.31 g (11.3 mmol) of methyl 3-methoxyacrylate were dissolved in 15 ml of dimethylsulfoxide, and 1.70 g (11.3 mmol) of trifluoromethanesulfonic acid was added to this solution at room temperature. Then, this solution was reacted for one hour with stirring in an oil bath at 90° C.

After completion of the reaction, the obtained reaction solution was poured into 100 ml of ice water and extracted with diethyl ether. The organic layer was dried over anhydrous sodium sulfate, and the solvent was distilled off under reduced pressure. The residue was purified by silica gel column chromatography to obtain 0.92 g (yield: 38.2%) of the reaction product. The obtained reaction product was confirmed to be identical with the reaction product of Example 9 by gas chromatography.

EXAMPLE 12

Step of condensation reaction 1.50 g (10.8 mmol) of 4-amino-1,1,1-trifluoro-3-buten-2-one and 1.31 g (11.3 mmol) of methyl 3-methoxyacrylate were dissolved in a solvent mixture comprising 5 ml of N,N-dimethylformamide and 10 ml of toluene, and 1.70 g (11.3 mmol) of trifluoromethanesulfonic acid was added to this solution at room temperature. Then, this solution was reacted for one hour with stirring in an oil bath at 90° C.

After completion of the reaction, the obtained reaction solution was poured into 100 ml of ice water and extracted with diethyl ether. The organic layer was dried over anhydrous sodium sulfate, and the solvent was distilled off under reduced pressure. Then, the residue was purified by silica gel column chromatography to obtain 1.02 g (yield: 42.3%) of the reaction product. The obtained reaction product was confirmed to be identical with the reaction product of Example 9 by gas chromatography.

EXAMPLE 13

Step of condensation reaction 1.50 g (10.8 mmol) of 4-amino-1,1,1-trifluoro-3-buten-2-one and 1.31 g (11.3 mmol) of methyl 3-methoxyacrylate were dissolved in 15 ml of N,N-dimethylformamide, and 1.70 g (11.3 mmol) of trifluoromethanesulfonic acid was added to this solution at room temperature. Then, this solution was reacted for one hour with stirring in an oil bath at 60° C.

After completion of the reaction, the obtained reaction solution was poured into 100 ml of ice water and extracted with diethyl ether. The organic layer was dried over anhydrous sodium sulfate, and the solvent was distilled off under reduced pressure. Then, the residue was purified by silica gel column chromatography to obtain 0.42 g (yield: 17.4%) of the reaction product. The obtained reaction product was confirmed to be identical with the reaction product of Example 9 by gas chromatography.

EXAMPLE 14

Step of condensation reaction 1.50 g (10.8 mmol) of 4-amino-1,1,1-trifluoro-3-buten-2-one and 1.31 g (11.3 mmol) of methyl 3-methoxyacrylate were dissolved in a solvent mixture comprising 5 ml of N,N-dimethylformamide, and 10 ml of toluene, and 1.70 g (11.3 mmol) of trifluoromethanesulfonic acid was added to this solution at room temperature. Then, this solution was reacted for two hours with stirring in an oil bath at 60° C.

After completion of the reaction, the obtained reaction solution was poured into 100 ml of ice water and extracted with diethyl ether. The organic layer was dried over anhydrous sodium sulfate, and the solvent was distilled off under reduced pressure. Then, the residue was purified by silica gel column chromatography to obtain 1.02 g (yield: 42.3%) of the reaction product. The obtained reaction product was confirmed to be identical with the reaction product of Example 9 by gas chromatography.

EXAMPLE 15

Step of condensation reaction 1.50 g (10.8 mmol) of 4-amino-1,1,1-trifluoro-3-buten-2-one and 1.31 g (11.3 mmol) of methyl 3-methoxyacrylate were dissolved in a solvent mixture comprising 5 ml of N,N-dimethylformamide and 10 ml of toluene, and 1.95 g (11.3 mmol) of paratoluenesulfonic acid was added to this solution at room temperature. Then, this solution was reacted for two hours with stirring in an oil bath at 90° C.

After completion of the reaction, the obtained reaction solution was poured into 100 ml of ice water and extracted with diethyl ether. The organic layer was dried over anhydrous sodium sulfate, and the solvent was distilled off under reduced pressure. Then, the residue was purified by silica gel column chromatography to obtain 0.48 g (yield: 19.9%) of the reaction product. The obtained reaction product was confirmed to be identical with the reaction product of Example 9 by gas chromatography.

EXAMPLE 16

Step of condensation reaction 1.50 g (10.8 mmol) of 4-amino-1,1,1-trifluoro-3-buten-2-one and 1.31 g (11.3 mmol) of methyl 3-methoxyacrylate were dissolved in a solvent mixture comprising 5 ml of N,N-dimethylformamide and 10 ml of toluene, and 1.09 g (11.3 mmol) of methanesulfonic acid was added to this solution at room temperature. Then, this solution was reacted for one hour with stirring in an oil bath at 90° C.

After completion of the reaction, the obtained reaction solution was poured into 100 ml of ice water and extracted with diethyl ether. The organic layer was dried over anhydrous sodium sulfate, and the solvent was distilled off under reduced pressure. Then, the residue was purified by silica gel column chromatography to obtain 0.89 g (yield: 36.9%) of the reaction product. The obtained reaction product was confirmed to be identical with the reaction product of Example 9 by gas chromatography.

EXAMPLE 17

Step of condensation reaction 2.00 g (14.4 mmol) of 4-amino-1,1,1-trifluoro-3-buten-2-one and 1.70 g (14.6 mmol) of methyl 3-methoxyacrylate were dissolved in 15 ml of toluene, and 560 mg (4.86 mmol) of 85% phosphoric acid was added to this solution at room temperature. Then, this solution was reacted for 18 hours with stirring in an oil bath at 60° C.

After completion of the reaction, the obtained reaction solution was poured into 100 ml of ice water and extracted with diethyl ether. The organic layer was washed with anhydrous sodium sulfate, and the solvent was distilled off under reduced pressure. Then, the residue was purified by silica gel column chromatography to obtain 1.09 g (yield: 34.0%) of the reaction product. The obtained reaction product was confirmed to be identical with the reaction product of Example 9 by gas chromatography.

EXAMPLE 18

Step of condensation reaction 2.00 g (14.4 mmol) of 4-amino-1,1,1-trifluoro-3-buten-2-one and 1.70 g (14.6 mmol) of methyl 3-methoxyacrylate were dissolved in 14 ml of dimethylsulfoxide, and 0.4 ml (7.2 mmol) of 98% concentrated phosphoric acid was added to this solution at room temperature. Then, this solution was reacted for 5 hours with stirring in an oil bath at 60° C.

After completion of the reaction, the obtained reaction solution was poured into 100 ml of ice water and extracted with diethyl ether. The organic layer was dried over anhydrous sodium sulfate, and the solvent was distilled off under reduced pressure. Then, the residue was purified by silica gel column chromatography to obtain 1.80 g (yield: 56.0%) of the reaction product. The obtained reaction product was confirmed to be identical with the reaction product of Example 9 by gas chromatography.

EXAMPLE 19

Step of condensation reaction

Into a 500 ml four-necked flask equipped with a thermometer, stirring vanes and a dropping funnel, 13.1 g (0.33 mol) of sodium hydride (60% oil suspension) and 140 ml of N,N-dimethylformamide were charged and cooled to a temperature of not higher than −5° C. by a cooling agent. Then, 72.2 g of a toluene solution containing 63.3% of 4-amino-1,1,1-trifluoro-3-buten-2-one (containing 0.33 mol of 4-amino-1,1,1-trifluoro-3-buten-2-one) was dropwise added thereto over a period of one hour and thirty minutes by a dropping funnel while maintaining the temperature at a level of not higher than −5° C. Then, 38.1 g (0.33 mmol) of methyl 3-methoxyacrylate was dropwise added over a period of 30 minutes by the dropping funnel while maintaining the temperature at a level of not higher than −5° C. After completion of the dropwise addition, the reaction solution was returned to room temperature (18° C.) and then further reacted for 1.5 hours with stirring at room temperature. Then, the obtained reaction solution was heated to 60° C., and toluene was distilled off under reduced pressure over a period of 30 minutes. Then, the reaction solution was left to cool.

The cooled reaction solution was poured into 840 ml of ice water, and then concentrated hydrochloric acid was added thereto so that the pH became about 3. The mixture was stirred for 30 minutes at a temperature of not higher than 5° C. The precipitated crystals were collected by filtration and washed with 140 ml of water. The obtained crystals were dried at 40° C. for 3 days to obtain 67.0 g (yield: 78.1%) of the reaction product.

The obtained reaction product was dissolved in deuterochloroform and NMR was measured, whereby a peak for N-2-methoxycarbonylvinyl 4,4,4-trifluoro-3-oxo-1-butenylamine was detected.

EXAMPLE 20

Step of condensation reaction

Into a 500 ml four-necked flask equipped with a thermometer, stirring vanes and a dropping funnel, 2.87 g (0.072 mol) of sodium hydride (60% oil suspension) and 30 ml of N,N-dimethylformamide were charged, and the mixture was cooled to a temperature of not higher than −5° C. by a cooling agent. Then, 10.0 g (0.072 mol) of 4-amino-1,1,1-trifluoro-3-buten-2-one (purity: 99.6%), 8.31 g (0.072 mol) of methyl 3-methoxyacrylate and 10 ml of toluene were dropwise added thereto over a period of one hour by a dropping funnel while maintaining the temperature to a level of not higher than −5° C. After completion of the dropwise addition, the reaction solution was reacted for further 30 minutes with stirring while maintaining the temperature at a level of not higher than −5° C. Then, the mixture was returned to room temperature (19° C.). After reacting it with stirring for 2 hours at room temperature, the obtained reaction solution was heated to 60° C., and toluene was distilled off under reduced pressure for one hour. Then, the reaction solution was left to cool.

The cooled reaction solution was poured into 180 ml of ice water. Then, concentrated hydrochloric acid was added so that the pH became about 3. The mixture was stirred for 30 minutes at a temperature of not higher than 5° C. The precipitated crystals were collected by filtration and washed with 100 ml of water. The obtained crystals were dried at 40° C. for 3 days to obtain 14.1 g (yield: 77.2%) of the reaction product.

The obtained reaction product was dissolved in deuterochloroform, and NMR was measured, whereby a peak for N-2-methoxycarbonylvinyl 4,4,4-trifluoro-3-oxo-1-butenylamine was detected.

EXAMPLE 21

Step of condensation reaction

Into a 500 ml four-necked flask equipped with a thermometer, stirring vanes and a dropping funnel, 4.0 g (0.10 mol) of sodium hydride (60% oil suspension) and 41.7 ml of tetrahydrofuran were charged, and the mixture was cooled to a temperature of not higher than −5° C. by a cooling agent. Then, 14.2 g (0.10 mol) of 4-amino-1,1,1-trifluoro-3-buten-2-one (purity: 98.1%) was dropwise added thereto over a period of 30 minutes by the dropping funnel, while maintaining the temperature at a level of not higher than −5° C. Then, 11.6 g (0.10 mol) of methyl 3-methoxyacrylate was dropwise added over a period of 30 minutes by the dropping funnel, while maintaining the temperature at a level of not higher than −5° C. After completion of the dropwise addition, the reaction solution was returned to room temperature (19° C.), and then it was reacted for 2 hours and 30 minutes with stirring at room temperature and further reacted for 30 minutes by an addition of 0.4 g (0.01 mol) of sodium hydride at room temperature.

After completion of the reaction, the obtained reaction solution was poured into 250 ml of ice water. Then, concentrated hydrochloric acid was added thereto so that the pH became about 3. The mixture was stirred at a temperature of not higher than 5° C. for 30 minutes. Precipitated crystals were collected by filtration and washed with 100 ml of water. The obtained crystals were dried at 40° C. for 3 days to obtain 20.1 g (yield: 73.6%) of the reaction product.

The obtained reaction product was dissolved in deuterochloroform, and NMR was measured, whereby a peak for N-2-methoxycarbonylvinyl 4,4,4-trifluoro-3-oxo-1-butenylamine was detected.

EXAMPLE 22

Step of ring closure and hydrolysis 7.94 g (0.036 mol) of N-2-methoxycarbonylvinyl 4,4,4-trifluoro-3-oxo-1-butenylamine was dissolved in 95 ml of methanol, and this solution was cooled with ice to a temperature of 5° C. Then, a solution having 1.64 g (0.071 mol) of metal sodium dissolved in 40 ml of methanol, was gradually dropwise added thereto. After completion of the dropwise addition, the reaction solution was returned to room temperature over a period of 30 minutes and then again heated and reacted for 3 hours and 45 minutes with stirring under heating and refluxing. Methanol was distilled off under reduced pressure. Then, a solution having 0.85 g (0.21 mol) of sodium hydroxide dissolved in 40 ml of water, was added to the residue, and the mixture was further reacted for 2 hours with stirring at room temperature.

After completion of the reaction, extraction was carried out by an addition of 50 ml of diethyl ether. The aqueous layer was acidified (pH 1 to 2) with concentrated hydrochloric acid. Then, the mixture was extracted again by an addition of 200 ml of diethyl ether. The ether layer was dried over anhydrous magnesium sulfate, and then the solvent was distilled off under reduced pressure to obtain 5.25 g (yield: 77%) of 4-trifluoromethylnicotinic acid (melting point: 145.9° C.).

Further, using N-2-methoxycarbonylvinyl 4,4,4-trifluoro-3-oxo-1-butenylamine obtained in Examples 8 to 21, ring closure and hydrolysis were carried out in accordance with Example 7(2) and Example 22, whereby 4-trifluoromethylnicotinic acid was produced.

EXAMPLE 23

(1) Step of condensation reaction 2,100 ml of an N,N-dimethylformamide solution containing 183 g (4.57 mol) of sodium hydride (60% oil suspension), was cooled with ice, and 706 g (5.08 mol) of 4-amino-1,1,1-trifluoro-3-buten-2-one was dropwise added thereto so that the temperature became not higher than −5° C. Then, this solution was heated, and 589 g (5.08 mol) of methyl 3-methoxyacrylate was dropwise added so that the temperature became not higher than 10° C. After completion of the dropwise addition, the mixture was stirred at room temperature for 2 hours.

After completion of the reaction, the obtained reaction solution was poured into 8,400 ml of ice water, and the mixture was stirred for 30 minutes at a temperature of not higher than 5° C. Further, dilute hydrochloric acid was added thereto so that the pH in ice water at the time of introduction of the reaction solution became 4 to 5. The precipitate was collected by filtration and washed with water. The obtained crystals were dried at 40° C. for 2 days to obtain 1,192 g of the reaction product (yield: 84.8%).

The obtained reaction product was dissolved in deuterochloroform, and NMR was measured, whereby in addition to a peak for N-1-methoxy-2-methoxycarbonylethyl 4,4,4-trifluoro-3-oxo-1-butenylamine, a peak for N-2-methoxycarbonylvinyl 4,4,4-trifluoro-3-oxo-1-butenylamine was detected.

A part of the reaction product thus obtained was isolated and purified by silica gel column chromatography to obtain N-1-methoxy-2-methoxycarbonylethyl 4,4,4-trifluoro-3-oxo-1-butenylamine having a melting point of from 68° to 70° C.

(2) Step of ring closure and hydrolysis 1,050 ml of a methanol solution containing 1,221 g (6.33 mol) of sodium methoxide (28 wt% methanol solution), was heated to 60° C., and 830 ml of a methanol solution containing 1,076 g (4.22 mol) of N-1-methoxy-2-methoxycarbonylethyl 4,4,4-trifluoro-3-oxo-1-butenylamine as the reaction product obtained in (1), was dropwise added thereto. After completion of the dropwise addition, the mixture was stirred for one hour under heating and refluxing. Then, 152 g (8.44 mol) of water was further added, and the mixture was heated and refluxed for 30 minutes.

After completion of the reaction, methanol was distilled off under reduced pressure, and 2,600 ml of water was added to the residue, and the mixture was washed with ethylene dichloride. The aqueous layer was acidified (pH 1 to 2) with diluted hydrochloric acid, and the precipitate was collected by filtration. The crystals obtained by filtration were dried for one day at 40° C. to obtain 651 g (yield: 78.1%) of 4-trifluoromethylnicotinic acid.

According to the process of the present invention, the compound of the formula (I) and the compound of the formula (II) are reacted in the presence of a base, whereby a compound of the formula (III) i.e. a 4-alkoxy-1,1,1-trifluoro-3-buten-2-one, can be produced in good yield in a short period of time. Further, by reacting the compound obtained by the above process, with ammonia, it is possible to produce 4-amino-1,1,1-trifluoro-3-buten-2-one of the formula (IV) in good yield by a simple reaction step.

According to the process of the present invention, the compound of the formula (IV) and the compound of the formula (II) are condensed to obtain a compound of the formula (III) or its salt, which is then subjected to ring closure and hydrolysis to readily obtain the desired product 4-trifluoromethylnicotinic acid or its salt. This reaction requires a less number of reaction steps as compared with the conventional reactions, whereby the desired product can be produced in good yield under mild reaction conditions.

What is claimed is:

1. A process for producing 4-trifluoromethylnicotinic acid of the formula (VIII) or its salt:

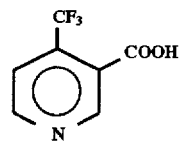   (VIII)

which comprises (i) a first step of reacting a halide of the formula (I):

   (I)

wherein Hal is a halogen atom, with a compound of the formula (II):

$CH_2=CHOR^1$   (II)

wherein $R^1$ is an alkyl group, in the presence of a base to obtain a 4-alkoxy-1,1,1-trifluoro-3-buten-2-one of the formula (III):

$CF_3CO-CH=CH-OR^1$   (III)

wherein $R^1$ is as defined above, and reacting this compound with ammonia to obtain 4-amino-1,1,1-trifluoro-3-buten-2-one of the formula (IV):

   (IV)

and (ii) a second step of subjecting the 4-amino-1,1,1-trifluoro-3-buten-2-one obtained in the first step and a compound of the formula (V):

$ACO_2R^2$   (V)

wherein $R^2$ is an ester-forming residue, and A is $(R^3O)CH=CH-$ or $(R^3O)_2CHCH_2-$, wherein $R^3$ is an alkyl group, to a condensation reaction to obtain a compound of the formula (VI) (inclusive of its salt):

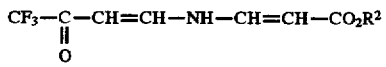   (VI)

wherein $R^2$ is as defined above, and/or a compound of the formula (VII) (inclusive of its salt):

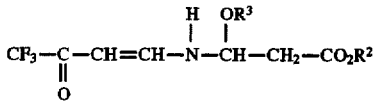   (VII)

wherein $R^2$ and $R^3$ are as defined above, as the reaction product, and then subjecting the reaction product to ring closure and hydrolysis.

2. A process for producing 4-trifluoromethylnicotinic acid of the formula (VIII) or its salt:

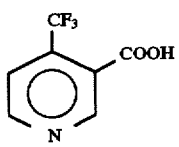

which comprises subjecting 4-amino-1,1,1-trifluoro-3-buten-2-one of the formula (IV):

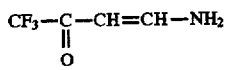 (IV)

and a compound of the formula (V):

 (V)

wherein $R^2$ is an ester-forming residue, and A is $(R^3O)CH=CH-$ or $(R^3O)_2CHCH_2-$, wherein $R^3$ is an alkyl group, to a condensation reaction to obtain a compound of the formula (VI) (inclusive of its salt):

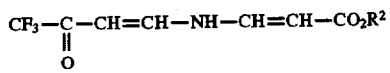 (VI)

wherein $R^2$ is as defined above, and/or a compound of the formula (VII) (inclusive of its salt):

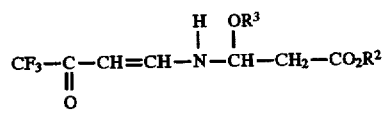 (VII)

wherein $R^2$ and $R^3$ are as defined above, as the reaction product, and then subjecting the reaction product to ring closure and hydrolysis.

3. The process according to claim 1, wherein the halide of the formula (I) is trifluoroacetyl chloride.

4. The process according to claim 1, wherein the compound of the formula (III) is reacted with ammonia without isolation.

5. The process according to claim 1, wherein the ammonia to be used for the reaction is ammonia gas.

6. The process according to claim 1, wherein a solvent is used for the reaction of the halide of the formula (I) with the compound of the formula (II).

7. The process according to claim 1, wherein the compound of the formula (IV) and a compound of the formula (V-1):

 (V-1)

wherein $R^2$ is an ester-forming residue, and $R^3$ is an alkyl group, are subjected to the condensation reaction.

8. The process according to claim 1, wherein the compound of the formula (IV) and a compound of the formula (V-2):

$(R^3O)CH=CHCO_2R^2$  (V-2)

wherein $R^2$ is an ester-forming residue, and $R^3$ is an alkyl group, are subjected to the condensation reaction in the presence of a base or an acid.

9. The process according to claim 7, wherein the condensation reaction is carried out in the presence of a base and/or a solvent.

10. The process according to claim 8, wherein the condensation reaction is carried out in the presence of a solvent.

11. The process according to claim 1, wherein the ring closure and the hydrolysis are carried out in the presence of a base and/or a solvent.

12. The process according to claim 1, wherein in the condensation reaction, the compound of the formula (V) is used in an amount of from 1.0 to 1.2 mols per mol of the compound of the formula (IV).

13. A process for producing 4-trifluoromethylnicotinic acid of the formula (VIII) or its salt:

 (VIII)

which comprises subjecting a compound of the formula (VI) (inclusive of its salt):

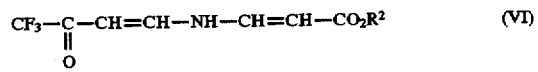 (VI)

wherein $R^2$ is an ester-forming residue, and/or a compound of the formula (VII) (inclusive of its salt):

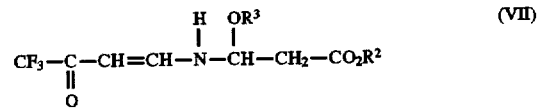 (VII)

wherein $R^2$ is as defined above and $R^3$ is an alkyl group, to ring closure and hydrolysis.

* * * * *